United States Patent [19]

Kauer

[11] 3,997,565
[45] Dec. 14, 1976

[54] ACYLCROWNETHER OXIMES AND OXIME ETHERS

[75] Inventor: James Charles Kauer, Kennett Square, Pa.

[73] Assignee: E. I. Du Pont de Nemours and Company, Wilmington, Del.

[22] Filed: Sept. 19, 1975

[21] Appl. No.: 615,185

[52] U.S. Cl. .............................. 260/340.3; 424/278
[51] Int. Cl.² ....................................... C07D 323/00
[58] Field of Search .................................. 260/340.3

[56] References Cited

UNITED STATES PATENTS 3,405,138  10/1968  Judd ................................. 260/340.3
3,687,978  8/1972   Pedersen ......................... 260/340.3

OTHER PUBLICATIONS

Pedersen, Journ. Amer. Chem. Society, 89, 7017–7036, (1967).
Kopolow et al., Macromolecules 6, 133–142, (1973).

Primary Examiner—Ethel G. Love
Attorney, Agent, or Firm—Anthony P. Mentis

[57] ABSTRACT

Certain acylcrownether oximes, oxime ethers and oxime esters are complexing agents for metals, dispersing agents for carbon black and antiviral agents. Exemplary is the oxime of 4-acetylbenzo-18-crown-6 of the formula

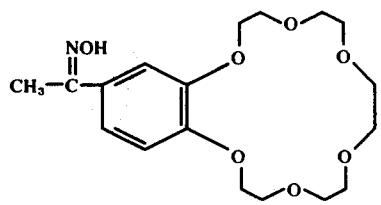

20 Claims, No Drawings

ACYLCROWNETHER OXIMES AND OXIME ETHERS

BACKGROUND OF THE INVENTION

1. Field of the Invention

Certain acylocrownether oximes and oxime ethers and esters are complexing agents for metals and dispersing agents for carbon black. Many of the compounds also show activity in vitro against a number of picornaviruses.

2. Prior Art

Pedersen J. Am. Chem. Soc. 89 7017 (1967) describes cyclic polyethers derived from aromatic vicinal diols by reaction with α,ω-alkylene diprimary dihalides containing oxygen atoms in the chain in the presence of strong bases. In particular, when catechol, sodium hydroxide and 1,14-dichloro-3,6,9,12-tetraoxatetradecane are reacted, there is obtained the compound

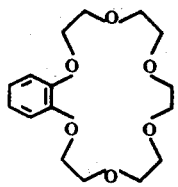

2,3-benzo-1,4,7,10,13,16-hexaoxacyclooctadec-2-ene. This compound is named 2,3,5,6,8,9,11,12,14,15-decahydro-1,4,7,10,13,16-benzohexaoxacyclooctadecin by Chemical Abstracts. A more convenient trivial terminology, which is employed herein, is to identify the compound as a "crown" compound wherein the total number of atoms in the macrocylic ring is designated by an antecedent number and the total number of oxygen atoms by a subsequent number. Using this terminology, the above compound is called benzo-18-crown-6.

Kopolow et al., Macromolecules 6 133 (1973) have described the 4-acetyl derivative of benzo-18-crown-6.

DESCRIPTION OF THE INVENTION

The invention is a compound of the general formula

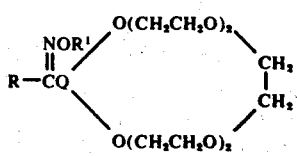

wherein
R is hydrogen, alkyl of 1–10 carbons, aryl of 6–10 carbons, aralkyl of 7–10 carbons, heterocyclic of 5–6 ring atoms containing 1 or 2 nitrogen, sulfur or oxygen atoms in the ring, and such groups containing up to two substituents of fluorine, chlorine, bromine, nitro, amino or alkoxy of 1–10 carbons;
R$^1$ is hydrogen, alkyl of 1–10 carbons or aminoalkyl 1–7 carbons including mono- and dialkylamino, morpholinoalkyl and pyrrolidinylalkyl or acyl of 1–10 carbons in which acyl is an alkylcarbonyl, arylcarbonyl (including aralkylcarbonyl) group or such groups containing up to 2 fluorine, chlorine or methoxyl substituents;

Q is

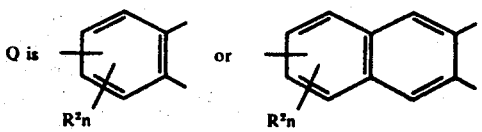

in which
R$^2$ is hydrogen, fluorine, chlorine, bromine, nitro, amino or alkyl of 1–10 carbons; n 0 to 2; and R and R$^2$ together can be a polymethylene, —(CH$_2$)—$_{3,4,5,}$ or $_6$. group.

Alkyl includes straight, branched and cyclic alkyl groups including, for example, methyl, ethyl, propyl, butyl, hexyl, octyl, decyl, isopropyl, isobutyl, isooctyl, cyclopropyl, cyclobutyl, methylcyclopropyl, methylcyclobutyl, ethylcyclopropyl, ethylcyclobutyl and the like.

Aryl is exemplified by phenyl, biphenyl and naphthyl, etc.

Aralkyl includes benzyl, phenethyl, and the like.

Heterocyclic of 5–6 ring atoms containing one or two nitrogen, sulfur or oxygen atoms includes pyridyl, pyrazyl, thienyl, furyl, dioxolyl, and the like.

The general formula above can also be written more pictorially as

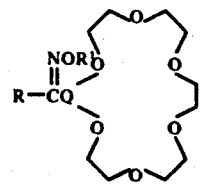

Preferred are compounds where R is an alkyl group of 1–12 carbons and R$^2$ is hydrogen or an alkyl group of 1–6 carbons on the 5-position of a benzo ring when Q=benzo or the 7-position of a naphtho ring when Q=naphtho. Most preferred are compounds where R$^2$ is hydrogen.

The most preferred compounds for antiviral activity are those where R is methyl, ethyl or propyl; R$^1$ is methyl, ethyl, benzyl, benzoyl or acetyl; and R$^2$ is H in compunds of the formula

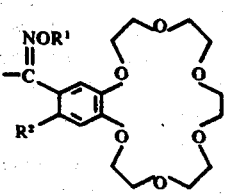

The compounds of the invention are useful as dispersing agents for carbon black and complexing agents for metals. They can also be employed as the polycyclic ethers in the process of U.S. Pat. No. 3,546,318 to provide improved scratch resistant coatings.

The most preferred compounds are capable of preventing the infection of HeLa cells in vitro by a wide spectrum of picornaviruses and in particular rhinoviruses.

The oximes or oxime ethers are obtained by reaction of an acylated benzo-18-crown-6 with hydroxylamine or an alkoxy- or aralkoxy-amine. The acylated compounds result from acylation of benzo-18-crown-6 itself or a 4-lower alkyl derivative (on the benzenoid ring). The latter compounds are prepared by using a substituted catechol (e.g., 4-n-amyl-1,2dihydroxybenzene instead of catechol in the crown forming reaction mentioned above.

The oxime esters can be obtained by treatment of the oxime with acid chlorides. The alkoxy (or aralkoxy) amines may be prepared by treatment of the corresponding alkyl (or aralkyl) bromide with a sodium or potassium salt of acetone oxime or N-hydroxyurethane followed by acid hydrolysis.

The aromatic halogen substituents may be introduced by a direct halogenation procedure, or from the corresponding amine, followed by diazotization with nitrous acid and decomposition of the fluorborate salt or cuprous bromide or chloride treatment.

The amino derivations may be prepared by conventional catalytic hydrogenation of the corresponding nitro compounds. The latter can be obtained by direct nitration of the acylated benzo-18-crown-6. The nitro group may also be introduced into the catechol used as a starting material for crown ether ring closure.

SPECIFIC EMBODIMENTS OF THE INVENTION

In the following illustrative examples all parts are by weight and all temperatures are Centigrade unless otherwise specified. The processes shown in the examples can be used to prepare all the compounds of the general formula.

EXAMPLE 1

4'-Acetylbenzo-18-crown-6 Oxime
[2,3,5,6,8,9,11,12,14,15-Decahydro-18-(1-hydroxyiminoethyl)-
1,4,7,10,13,16-benzohexaoxacyclooctadecin]

a. 4-Acetylbenzo-18-crown-6

This compound was prepared by the direct acetylation of benzo-18-crown-6 as follows:

In a 1-liter 3-neck flask with mechanical stirrer a suspension of 32.0 g (0.24 mole) of anhydrous aluminum chloride in 500 ml of dry 1,2-dichloroethane (DCE) was cooled in an ice bath and a solution of 15.7 g (0.20 moles) of acetyl chloride in 50 ml of 1,2-dichloroethane was added. Subsequently, a solution of 25 g (0.080 moles) of benzo-18-crown-6 [C J. Pedersen, J. Am. Chem. Soc., 89, 7017 (1967)] in 50 ml of 1,2-dichloroethane was added. The mixture was stirred 2 days and then treated with 150 g of ice. After 30 min., the organic layer was separated, the water layer was extracted with methylene chloride, and the combined organic layers were stirred overnight with 10% aqueous potassium carbonate. The mixture was filtered, the organic layer was separated, dried (MgSO$_4$), and solvent was removed under reduced pressure.

The resulting oily product crystallized and was stirred with several portions of pentane totalling 800 ml to remove unreacted benzo-18-crown-6. The white solid residue was recrystallized from 2 liters of hexane to produce 19.0 g (67%) of acetylbenzo-18crown-6 in two crops.

b. 4-Acetylbenzo-18-crown-6 Oxime

A mixture of 0.527 g of acetylbenzo-18-crown-6, 0.6 g of hydroxylamine hydrochloride, 3 ml of pyridine and 3 ml of ethanol was sealed in a bottle and heated in a steam bath for 1.5 hr at 100° C. The solvent was evaporated under reduced pressure. The residue was dissolved in 10 ml of water and was continuously extracted with ether for 4 hr. The extract, on evaporation, yielded 0.197 g of white crystals which were recrystallized from 7 ml of ethanol to which 7 ml of pentane was added. The white crystalline product melted at 110.5°–111.5° C.

Anal. Calcd for $C_{18}H_{27}NO_7$: C, 58.52; H, 7.37; N, 3.79. Found: C, 59.01; H, 7,32; N, 3.68; C, 58.61; 58161; H, 7.25; N, 3.56.

The oxime reacted with water to form a monohydrate, which melted at 100°–105° C.

Anal. Calcd for $C_{18}H_{29}NO_8$: C, 55.80; H, 7.55; N, 3.62. Found: C, 56.27; H, 7.24; N, 3.52.

After standing for 5 days in dry air or after vacuum drying at 80° C, the water of hydration was lost.

Better yields resulted when a mixture of 22.8 g of acetylbenzo-18-crown-6, 125 ml of ethanol, 75 ml of dry pyridine, and 20 g of hydroxylamine hydrochloride was heated under reflux on the steam bath for 3 hr. After purification as above and two recrystallizations from ethanol the product (18.13 g) melted at 115.4°–116.0° c.

EXAMPLE 2

4'-Acetylbenzo-18-crown-6 Oxime O-Methyl ether
[2,3,5,6,8,9,11,12,14,15-Decahydro-18-(1-methoxyiminoethyl)-
1,4,7,10,13,16-benzohexaoxacyclooctadecin]

A mixture of 5.0 g of acetylbenzo-18-crown-6, 5.0 g of methoxyamine hydrochloride, 15 ml of pyridine, and 25 ml of ethanol was heated under reflux on the steam bath for 3 hr. Solvent was removed under reduced pressure from the resulting reaction product. The residue in 100 ml of water was continuously extracted with ether to yield 5.3 g of white solid which on recrystallization from 500 ml of hexane produced 3.747 g of white crystals, mp 79.0°–79.8°.

Anal. Calcd for $C_{19}H_{29}NO_7$: C, 59.51; H, 7.62; N, 3.65. Found: C, 59.38; H, 7.59; N, 3.43.

EXAMPLE 3

4'-Acetylbenzo-18-crown-6 Oxime O-Benzyl ether
[2,3,5,6,8,9,11,12,14,15-Decahydro-18-(1-benzyloxyiminoethyl)-
1,4,7,10,13,16-benzohexaoxacyclooctadecin]

A mixture of 14.20 g of acetylbenzo-lb 18-crown-6, 4.90 g of benzyloxyamine and 0.1 g of ammonium chloride was sealed in a Carius tube and heated overnight in the steam bath. The resulting viscous oil was dissolved in 100 ml of benzene and decanted from the small amount of insoluble residue. Solvent was removed from the benzene solution under reduced pressure, and the residual oil was stirred with 200 ml of hexane. It crystallized rapidly, was filtered, and was washed with hexane. The whitish crystalline product was dissolved in 75 ml of benzene. Hexane (200 ml) was added to the incipient cloud point. Activated charcoal (Darco) was then added, the solution was filtered, and additional hexane was added to the incipient cloud point. The solution was seeded and deposited 6.4 g of fine platelets. Recrystallization from 40 ml of ethanol produced 5.31 g of white crystals which melted at 65.5°–68.2°. (An additional 1.44 g was obtained by reprocessing the residues.)

Anal. Calcd for $C_{25}H_{33}NO_7$: C, 65.34; H, 7.24; N, 3.05. Found: C, 65.53; H, 7.29; N, 3.14; C, 65.19; H, 7.35.

EXAMPLE 4

4'-Acetylbenzo-18-crown-6 Oxime O-(γ-propyl-1-morpholino)ether Dihydrate [2,3,5,6,8,9,11,12,14,15-Decahydro-18-(-1-[-3-(4-morpholinyl propoxyimino]ethyl)-1,4,7,10,13,16-benzohexaoxaoyclooctadecin]

A mixture of 3-N-morpholinopropyl-1oxyamine, 3.5 ml of dry pyridine, 3.63 g of 4-acetylbenzo-18-crown-6, and 10 ml of ethanol was heated on the steam bath for 3 hr. The solution was allowed to stand overnight, and solvent was removed under reduced pressure. The residue was dissolved in 20 ml of water and unreacted acetylbenzo-18-crown-6 was removed by continuous extractions with ether and with benzene. The aqueous layer was then extracted with methylene chloride for 2 days. The methylene chloride extract was separated and solvent was removed under reduced pressure to leave a colorless oil (4.91 g) which solidified when triturated with 25 ml of pentane. The crystalline product was recrystallized from 15 ml of ethanol to which 50 ml of hexane and 50 ml of benzene was added. The resulting white crystalline flakes melted at 112.8°–114°.

Anal. Calcd for $C_{25}H_{40}N_2O_{10}$: C, 56.37; H, 8.33; N, 5.26. Found: C, 56.23; H, 7.82; N, 5.24; C, 56.32; H, 7.45; N, 5.16.

EXAMPLE 5

4'-Butyrylbenzo-18-crown-6 Oxime [1-(2,3,5,6,8,9,11,12,14,15-Decahydro-1,4,7,10,13,16-benzohexacyclooctadecin-18-yl)-1-butanone Oxime]

a. 4'-Butyrylbenzo-18-crown-6

A stirred suspension of 4.953 g of anhydrous aluminum chloride in 100 ml of dry 1,2-dichloroethane was cooled in ice and a solution of 4.066 g of n-butyryl chloride in 10 ml of 1,2-dichloroethane was added followed by a solution of 3.668 g of benzo-18-crown-6 in 50 ml of 1,2-dichloroethane. The mixture was stirred three days, and the reddish complex was decomposed by the addition of ice (30 g total). The organic layer was separated. The water layer was extracted with methylene chloride. The combined organic layers were stirred with 10% aqueous potassium carbonate solution for 2 hr, dried over magnesium sulfate, and evaporated. The residual oil crystallized. The resulting solid was triturated with 50 ml of pentane filtered, and was then recrystallized from 600 ml of boiling hexane to produce white crystals which melted at 57.9°–58.9°.

Anal. Calcd for $C_{20}H_{30}O_7$: C, 62.81; H, 7.91. Found: C, 63.14; H, 7.96; C, 63.15; H, 7.91.

b. 4'-Butyrylbenzo-18-crown-6 Oxime

A mixture of 1.028 g of 4'-butyrylbenzo-18-crown-6, 1.031 g of hydroxylamine hydrochloride, 6 ml of ethanol and 4 ml of pyridine was heated to reflux for 3 hr. Solvent was removed under reduced pressure, and the residue was dissolved in 20 ml of water and continuously extracted with ether. The ether extract was evaporated to leave 1.195 g of a colorless oil which crystallized. It was recrystallized from a 2:1 hexane/ethanol mixture to give 0.716 g of white solid. Recrystallization produced white crystals which melted at 104.0°–105.1°.

Anal. Calcd for $C_{20}H_{31}NO_7$: C, 60.44; H, 7.86; N, 3.52, Found: C, 60.59; H, 7.95; N, 3.54.

EXAMPLE 6

4'-Benzoyl-18-crown-6 Oxime [2,3,5,6,8,9,11,12,14,15-Decahydro-18-(1-hydroxyimino-1-phenyl methyl)-1,4,7,10,13,16-benzohexaoxacyclooctadecin]

A mixture of 1.01 g of 4'-benzoyl-18-crown-6, 1.03 g of hydroxylamine hydrochloride, 3 ml of pyridine and 5 ml of ethanol was heated to reflux for 4 hr. Solvent was removed under reduced pressure, and the residue was dissolved in 30 ml of water. Flocculent white solid precipitated and was filtered off and triturated with 5% aqueous hydrochloric acid. The solid was filtered, washed with water, was dried and was recrystallized from 10 ml of ethanol to which 20 ml of hexane was added.

The product was isolated as a dihydrated complex with a mole of hydroxylamine and melted at 209°–210°.

Anal. Calcd for $C_{23}H_{29}NO_7 \cdot NH_2OH \cdot 2H_2O$: C, 55.19; H, 7.25; N, 5.60. Found: C, 54.71; H, 6.70; C, 54.78; H, 6.54; N, 5.40; N, 5.55.

EXAMPLE 7

4'-benzoylbenzo-18crown-6 Oxime O-Methyl Ether [2,3,5,6,8,9,11,12,14,15-Decahydro-18-(1-methoxyimino-1-phenyl methyl)-1,4,7,10,13,16-benzohexaoxacyclooctadecin]

A mixture of 1.00 g of 4'-benzoylbenzo-18-crown-6, 1.00 g of methoxyamine hydrochloride, 3 ml of pyridine, and 5 ml of ethanol was heated in a sealed bottle in the steam bath for 2 hr. Solvents were evaporated from the product, and the residue in 20 ml of water was continuously extracted with ether for 3 hr. The ether extract was stripped under reduced pressure, and the residue (1.037 g) was allowed to crystallize under 30 ml of pentane. The resulting fine white powder (0.920 g) was filtered and recrystallized from aqueous ethanol to yield 364 mg of fine needles, mp 69.8°–70.9°.

Anal. Calcd for $C_{24}H_{31}NO_7$: C, 64.70; H, 7.01; N, 3.14, Found: C, 64.77; H, 7.02; N, 3.12.

EXAMPLE 8

4'-Benzoylbenzo-18-crown-6 Oxime O-Benzyl Ether [2,3,5,6,8,9,11,12,14,15-Decahydro-18-(1-phenyl-1-phenylmethoxyiminomethyl)-1,4,7,10,13,16-benzohexaoxacyclooctadecin]

A mixture of 2.08 g of 4'-benzoylbenzo-18-crown-6 and 0.611 g benzyloxyamine was sealed in a small glass tube with 1 mg of ammonium chloride. The mixture was heated overnight in the steam bath. It was then diluted with 3 ml of ethanol and 0.11 g of additional benzyloxyamine was added. The solution was sealed in a glass tube and heated at 150° overnight. The infrared spectrum of the resulting product indicated that some unreacted benzoylbenzo-18-crown-6 remained. About one half of this material was then heated overnight at 170° with 0.070 g of additional benzyloxyamine. Solvent and unreacted benzyloxyamine was removed under reduced pressure. The resulting product was a viscous colorless oil. When stirred with water the oil crystallized to form a white hydrate which, however, readily lost water when allowed to stand in dry air. The infrared spectrum of these crystals in chloroform solution exhibited absorptions at 3500, 3580, and 3650 cm⁻¹ (ascribed to water) and 1610 and 1640 cm⁻¹ (aromatic and C=N absorptions).

EXAMPLE 9

4'-Formylbenzo-18-crown-6 Oxime
[2,3,5,6,8,9,11,12,14,15-Decahydro-18-(1-hydroxyiminomethyl)-1,4,7,10,13,16-benzohexaoxacyclooctadecin]

a. 4'-Formylbenzo-18-crown-6

Titanium tetrachloride (50 g.) was added dropwise at 0° to a solution of 15.6 g of benzo-18-crown-6 in 200 ml of 1,2-dichloroethane. Then a solution of 1,1-dichloromethyl methyl ether in 1,2-dichloroethane was added dropwise at 0°. After stirring 36 hrs. at room temperature, ice was added. The organic layer was separated and the water layer was extracted with methylene chloride. The combined organic layers were dried (MgSO₄), stripped of solvent, and the residue stirred with 50 ml of ether. The resulting cream colored solid was recrystallized from 300 ml of 5:1 hexane/ethanol to give 5.86 g of crystals mp. 61°–62°, after washing with ether.

Anal. Calcd for C₁₇H₂₄O₇: C, 59.99; H, 7.11, Found: C, 59.85; H, 7.41.

b. 4'-Formylbenzo-18-crown-6 Oxime

A suspension of 4.0 g (0.03 mol) of aluminum chloride in 50 ml of DCE was stirred under nitrogen and cooled in an ice bath. A solution of 2.57 g (0.033 mol) of acetyl chloride in 25 ml of DCE was added dropwise. The mixture, which was almost clear, was stirred for 1 hr at 0°, then allowed to warm to room temperature. A solution of 3.26 g (0.01 mol) of 4'-methylbenzo-18-crown-6 [U. Takaki, T. E. Hogen-Esch, J. Smid, *Am. Chem. Soc.*, 93, 6760 (1971)] was added dropwise in 25 ml of DCE. Stirring was continued for 2 days. The resulting green solution was poured into water and extracted three times with methylene chloride. The organic layers were washed three times with saturated brine, dried over magnesium sulfate and stripped to give 4.0 g of a light yellow oil which crystallized on standing. Crystallization from hexane (decanting from an oil) gave 1.5 g (41%) of white plates, mp 62°–64°. Triturating the mother liquors from above with petroleum ether gave an additional 1.1 g (30%) of the product, mp 66°–70°. Further recrystallization and vacuum drying at 56° gave an analytical sample, mp 64.5°–66.5°; infrared (nujol) 1685 (C=O), 1600 (aromatic C=C), 1025 (C—O—C) cm⁻¹; nmr CCOCl₃) 2.50 (d, 6H, —CH₃ and COCH₃), 3.66 (s), 3.75 (s), 4.05 (m, total 20H, macro ring), 6.70 (s, 1H), and 7.30

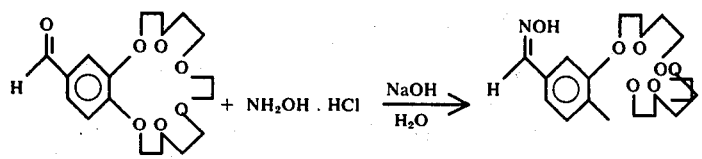

4'-Formylbenzo-18-crown-6 (0.6 g, 1.8 mmol) was dissolved in 1.5 g of hydroxylamine hydrochloride, 9 ml of water and 6 ml of 2N sodium hydroxide solution. This mixture was heated on a steam bath for ¾ hr. The mixture was extracted three times with ethyl acetate, washed once with water, dried (magnesium sulfate) and stripped to give 0.3 g of a white solid, mp 135°–137°. Further extraction of the water layers with methylene chloride gave an additional 0.3 g of product. The two fractions were combined and recrystallized from ethyl acetate to give 0.57 g (91%) fluffy white needles, mp 139°–141°. An analytical sample, mp 138.5°–139°, was prepared by further recrystallization; infrared (nujol) 3350 (–OH), 1605, 1580 (aromatic C=C and/or C=N), 1150 (ArOC), 1050 (COC) cm⁻¹.

Anal. Calcd for C₁₇H₂₅NO₇: C, 57.45; H, 7.09; N, 3.94. Found: C, 57.80; H, 7.21; N, 3.77.

EXAMPLE 10

4'-Acetyl-5'-Methylbenzo-18-crown-6 Oxime
[2,3,5,6,8,9,11,12,14,15-Decahydro-18-(1-hydroxyiminoethyl)-19-methyl-1,4,7,10,13,16-benzohexaoxacyclooctadecin]

a. 4'-Acetyl-5'-methyl-18-crown-6

(s, 1H, aromatic protons).

Anal. Calcd for C₁₉H₂₈O₇: C, 61.94; H, 7.66. Found: C, 61.53; H, 7.52; C, 61.74; H, 7.64.

b. 4'-Acetyl-5'-methylbenzo-18-crown-6 Oxime

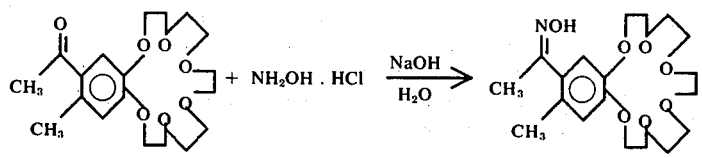

A solution of 6 g of hydroxylamine hydrochloride in 30 ml of water and 24 ml of 2N sodium hydroxide was prepared. 4'-Acetyl-5'-methylbenzo-18-crown-6 (2.4 g) was added and the solution heated on a steam bath for 1 hr. The mixture was cooled and extracted three times with ethyl acetate. The extracts were dried over magnesium sulfate and stripped to give 1.0 g of a colorless oil. Crystallization by slow cooling of an ether-hexane solution gave 0.78 g of white solid, mp 60°–81°. Recrystallization from ether-petroleum ether, then ether gave 0.4 g (16%), mp 86°–87.5°; infrared (neat) 3300 (—OH), 1605 (aromatic C=C) 1130 (ArOC), 1065 (COC) cm⁻¹.

Anal. Calcd for C₁₉H₂₉NO₇: C, 59.52; H, 7.62; N, 3.65. Found: C, 59.55; H, 7.70; N, 3.52.

Examples 11–22 described in Table I below were prepared by the processes of the previous examples.

TABLE I

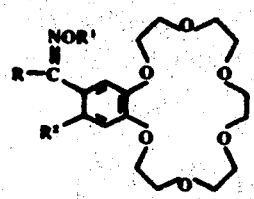

| Example No. | R | R' | R² | mp° C | Elemental Analysis For | Calcd | Found |
|---|---|---|---|---|---|---|---|
| 11 | CH₂-CH-CH₂ (cyclopropyl) | H | H | 64.4–66.8 | C<br>H<br>N | 60.74<br>7.39<br>3.54 | 60.74<br>7.42<br>3.66 |
| 12 | C₂H₅ | H | H | 77.1–81.8 | C<br>H<br>N | 59.51<br>7.62<br>3.65 | 60.01<br>7.76<br>3.90 |
| 13 | CH₂-CH₂-CH₂- (cyclopentano) | H | (See R) | 124–126 | C<br>H<br>N | 59.83<br>7.14<br>3.67 | 60.07<br>7.26<br>3.61 |
| 14 | CH₂-(CH₂)₄-CH (cyclohexyl) | H | H | 128–130.1 | C<br>H<br>N | 63.14<br>8.06<br>3.20 | 63.33<br>8.28<br>3.29 |
| 15 | CH₃ | (CH₃)₃C | H | 62.7–64.9 | C<br>H<br>N | 60.91<br>7.78<br>3.09 | 62.00<br>7.64<br>3.62 |
| 16 | H | CH₃ | H | 81.5–82 | C<br>H<br>N | 58.52<br>7.37<br>3.79 | 58.68<br>7.15<br>3.80 |
| 17 | CH₃ | C₂H₅ | H | 71.2–73.4 | C<br>H<br>N | 60.44<br>7.86<br>3.52 | 60.59<br>7.66<br>3.57 |
| 18 | CH₃ | n-C₆H₁₃ | H | 46.6–48.5 | C<br>H<br>N | 63.55<br>8.67<br>3.09 | 63.48<br>8.58<br>3.17 |
| 19 | CH₃ | n-C₁₀H₂₁ | H | 41.7–42.6 (Monohydrate) | C<br>H<br>N | 63.73<br>9.36<br>2.65 | 63.96<br>9.30<br>3.11 |
| 20 | CH₃ | CH₃C(O)— | H | 65.6–66.7 | C<br>H<br>N | 58.38<br>7.10<br>3.40 | 58.68<br>7.09<br>3.34 |
| 21 | CH₃ | C₆H₅C(O)— | H | 65.5–80.3 (monohydrate) | C₂₅H₃₃NO₉<br>C<br>H<br>N | 61.09<br>6.77<br>2.85 | 61.24<br>6.73<br>3.18 |
| 22 | C₆H₅ | H | CH₃ (3'-position) | 123–125 | | | |

The compounds of the preceding table can be named as follows:
11. 4'-cyclopropylcarbonylbenzo-18-crown-6 oxime or (2,3,5,6,9,11,12,14,15-decahydro-1,4,7,10,13,16-benzohexaoxacyclooctadecin-18-yl) (cyclopropyl)methanone oxime,
12. 4'-propionylbenzo-18-crown-6 oxime or 1-(2,3,5,6,8,9,11,12,14,15-decahydro-1,4,7,10,13,16-benzohexaoxacyclooctadecin-18-yl)-1-propanone oxime.
13. 4':5'-cyclopentanobenzo-18-crown-6 α-ketoxime,
14. 4'-cyclohexanecarbonylbenzo-18-crown-6 oxime,
15. 4'-acetylbenzo-18-crown-6 oxime pivaloate,
16. 4'-formylbenzo-18-crown-6 oxime methyl ether,
17. 4'-acetylbenzo-18-crown6 oxime ethyl ether or 2,3,5,6,8,9,11,12,14,15-decahydro-18-(1-ethoxyiminoethyl)-1,4,7,10,13,16-benzohexaoxacyclooctadecin,
18. 4'-acetylbenzo-18crown-6 oxime n-hexyl ether or 2,3,5,6,8,9,11,12,14,15-decahydro-18-(1-ethoxyiminoethyl)-1,4,7,10,13,16-benzohexaoxacyclooctadecin,
19. 4'-acetylbenzo-18-crown-6 oxime n-decyl ether or 2,3,5,6,8,9,11,12,14,15-decahydro-18-(1-decyloxyiminoethyl)-1,4,7,10,13,16-benzohexaoxacyclooctadecin,
20. 4'-acetylbenzo-18-crown-6 oxime acetate,
21. 4'-acetylbenzo-18-crown-6 oxime benzoate, and
22. 4'-benzoyl-3'-methylbenzo-18-crown-6 oxime.

EXAMPLE 23

6'-Acetyl-2:3-naphtho-18-crown-6 oxime [1-(2,3,5,6,8,9,11,12,14,15-decahydronaphtho[2,3-b]-1,4,7,10,13,16-hexaoxacyclooctadecin-16-yl)-ethanone, oxime ]

The general procedure of Example 1 was used with the acetylnapho-18-crown-6 to give the oxime, mp 138.1°–140.2°.

Anal: Calcd: C, 62.99; H, 6.97; N, 3.34, Found: C, 63.08; H, 6.99; N, 3.29.

Table II illustrates other compounds of the invention available by the general procedures of the preceding examples.

TABLE II

Structure: benzo-18-crown-6 with substituents $R-C(=NOR^1)-$ and $R^2$ on the benzene ring.

| Compound | R | $R^1$ | $R^2$ | Obtained From |
|---|---|---|---|---|
| 4′-Propionylbenzo-18-crown-6 oxime methyl ether | $C_2H_5$ | $CH_3$ | H | 4′-propionylbenzo-18-crown-6 and methoxyamine |
| 4′-cyclohexanecarbonylbenzo-18-crown-6 oxime ethyl ether | $C_6H_{11}$ | $C_2H_5$ | H | 4′-cyclohexanecarbonylbenzo-18-crown-6 and ethoxylamine |
| 4′-n-hexanoylbenzo-18-crown-6 oxime | $n\text{-}C_5H_{11}$ | H | H | 4′-hexanoylbenzo-18-crown-6 and hydroxylamine |
| 4′-n-undecanoylbenzo-18-crown-6 oxime | $n\text{-}C_{10}H_{21}$ | H | H | 4′-n-undecanoylbenzo-18-crown-6 and hydroxylamine |
| 4′-(4-chlorobutyryl)benzo-18-crown-6 oxime | $Cl(CH_2)_3$ | H | H | 4′-(4-chlorobutyryl)benzo-18-crown-6 and hydroxylamine |
| 4′-(3-fluoropropionyl)benzo-18-crown-6 oxime | $FCH_2CH_2$ | H | H | 4′-(3-fluoropropionyl)benzo-18-crown-6 and hydroxylamine |
| 4′-(2-phenylacetyl)benzo-18-crown-6 oxime | $C_6H_5CH_2$ | H | H | 4′-(2-phenylacetyl)benzo-18-crown-6 and hydroxylamine |
| 4′-acetylbenzo-18-crown-6 oxime, γ-dimethylaminopropyl ether | $CH_3$ | $(CH_3)_2 3)_2$ | H | 4′-acetylbenzo-18-crown-6 and γ dimethyl-aminopropoxyamine |
| 4′-acetylbenzo-18-crown-6 oxime, β-N-pyrrolidinoethyl ether | $CH_3$ | pyrrolidino-$CH_2CH_2$ | H | 4′-acetylbenzo-18-crown-6 and β-N-pyrrolidinoethoxyamine |
| 4′-acetylbenzo-18-crown-6 oxime, β-N-morpholino ethyl ether | $CH_3$ | morpholino-$CH_2CH_2$ | H | 4′-acetylbenzo-18-crown-6 and β-N-morpholinoethoxyamine |
| 4′-acetylbenzo-18-crown-6 oxime, n-decyl ether | $CH_3$ | $n\text{-}C_{10}H_{21}$ | H | 4′-acetylbenzo-18-crown-6 and n-decyloxyamine |
| 4′-acetylbenzo-18-crown-6 oxime, α-naphthylmethyl ether | $CH_3$ | α-naphthyl-$CH_2$ | H | 4′-acetylbenzo-18-crown-6 and α-naphthylmethoxyamine |
| 4′-acetyl-5′-chlorobenzo-18-crown-6 oxime | $CH_3$ | H | Cl | 4′-acetyl-5′-chlorobenzo-18-crown-6 and hydroxylamine |
| 4′-acetyl-5′-n-butylbenzo-18-crown-6 oxime | $CH_3$ | H | $n\text{-}C_4H_9$ | 4′-acetyl-5′-n-butylbenzo-18-crown-6 and hydroxylamine |
| 4′-α-pyridoylbenzo-18-crown-6 oxime | α-pyridyl | H | H | 4′-α-pyridoylbenzo-18-crown-6 and hydroxylamine |
| 4′-β-pyridoyl-5′-methylbenzo-18-crown-6 oxime | β-pyridyl | H | $CH_3$ | 4′-β-pyridoyl-5′-methylbenzo-18-crown-6 and hydroxylamine |
| 4′-β-thenoylbenzo-18-crown-6 oxime | β-thienyl | H | H | 4′-β-thenoylbenzo-18-crown-6 and hydroxylamine |
| 4′-α-thenoyl-5′-methylbenzo-18-crown-6 oxime | α-thienyl | H | $CH_3$ | 4′-α-thenoyl-5′-methylbenzo-18-crown-6 and hydroxylamine |
| 4′-α-furoylbenzo-18-crown-6 oxime | α-furyl | H | H | 4′-α-furoylbenzo-18-crown-6 and hydroxylamine |

TABLE II-continued

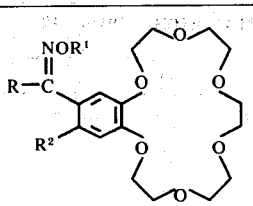

| Compound | R | R¹ | R² | Obtained From |
|---|---|---|---|---|
| 4'-β-furoyl-5'-methylbenzo-18-crown-6 oxime methyl ether | (furyl) | $CH_3$ | $CH_3$ | 4'-β-furoyl-5'-methylbenzo-18-crown-6 and methoxyamine |
| 4'-p-chlorobenzoyl-5'-methylbenzo-18-crown-6 oxime methyl ether | (p-Cl-phenyl) | $CH_3$ | $CH_3$ | 4'-p-chlorobenzoyl-5'-methylbenzo-18-crown-6 and hydroxylamine |
| 4'-o-fluorobenzoylbenzo-18-crown-6 oxime | (o-F-phenyl) | H | H | 4'-o-fluorobenzoylbenzo-18-crown-6 and hydroxylamine |
| 4'-benzoyl-5'-bromobenzo-18-crown-6 oxime | (phenyl) | H | Br | 4'-benzoyl-5'-bromobenzo-18-crown-6 and hydroxylamine |
| 4'-acetyl-5'-nitrobenzo-18-crown-6 oxime | $CH_3$ | H | $NO_2$ | 4'-acetylbenzo-18-crown-6 oxime nitrated |
| 4'-acetyl-5'-aminobenzo-18-crown-6 oxime | $CH_3$ | H | $NH_2$ | Reduction of nitro |
| 4'-β-naphthoylbenzo-18-crown-6 oxime | (naphthyl) | H | H | 4'-β-naphthoylbenzo-18-crown-6 and hydroxyamine |
| 4'-pyrazinecarbonylbenzo-18-crown-6 oxime | (pyrazinyl) | H | H | 4'-pyrazinecarbonylbenzo-18-crown-6 and hydroxylamine |

Also available are the following:
3'-β-pyridoylbenzo-18-crown-6 oxime; 3'-benzoylbenzo-18-crown-6 oxime; 6'-acetyl-2:3-naphtho-18-crown-6 oxime benzyl ether; 6'-benzoyl-2:3-naphtho-18-crown-6 oxime; 6'-acetyl-7'-methyl-2:3-naphtho-18-crown-6 oxime O-methyl ether; 4'-acetyl-5'-fluoro-6'methylbenzo-18-crown-6 oxime; 4'-acetyl-5'-methyl-3'-nitrobenzo-18-crown-6 oxime; and 4'-acetyl-5'-methyl-3'-aminobenzo-18-crown-6 oxime from the appropriate crown compound and hydroxylamino compound.

The most preferred compounds exhibit significant antiviral activity against all strains of human rhinoviruses when tested in tissue culture experiments as follows:

Cultured cells (usually HeLa, a human cell line) are grown to confluency in 60mm plastic petri dishes. Each culture is then infected with approximately 300 plaque-forming units of virus. Three different rhinovirus types (1A, 2, and 14) were used in all tests. The virus is allowed to adsorb to the cells for 30 minutes at 34.5° C.

Meanwhile, the compounds to be tested are dissolved in either ethanol or dimethylsulfoxide at a concentration 100 times greater than the highest concentration to be used in the test. (Compounds are tested in two-fold dilution steps from 200–12.5 μg/ml, but some compounds have been tested as low as 0.1 μg/ml.) The compound solution is then diluted 1:100 into a solution of McCoy's medium containing 5% heat-inactivated fetal calf serum and 0.38% agar. Two-fold dilutions are then made in the agar medium.

After the virus has adsorbed to the cells, excess virus is washed off and the cultures are overlaid with 5 ml of the agar medium containing the different compound concentrations. A control culture receives only agar medium. The cultures are incubated at 34.5° C for 2 to 5 days, depending on the virus used, to allow the development of plaques.

A plaque is a roughly circular area of dead cells in the culture, indicating the area where one plaque-forming unit of virus first infected one cell. The agar gel restricts the mobility of the virus so that the infection is contained and spreads out only from infected cell to neighboring cell.

When the plaques in the control culture are large enough to be seen easily but are still fairly discrete, all of the cultures are stained with 1% crystal violet. The plaques appear as clear spots against the deep purple of the uninfected cells. Toxic doses of compound will cause cells to detach from the plate and the cultures will take up less stain than the control culture. The compound-treated cultures are compared to the control culture for toxicity and for inhibition of plaques.

The activity level is the concentration of test chemical at which plaques are greatly reduced in size and number but are still partially visible (the virus "breakthrough" point). The toxicity level is the concentration of test chemical at which there is less intensity of purple color of the stained cultures compared to the controls. The various data for compounds of the invention are set out in Table III.

TABLE III

ACTIVITY AGAINST HUMAN RHINOVIRUS (HRV)

| Compound of Example | R | $R^1$ | $R^2$ | Q | Activity/Toxicity µg/ml | | |
|---|---|---|---|---|---|---|---|
| | | | | | HRV-1A | HRV-2 | HRV-14 |
| 1 | $CH_3$ | H | H | $C_6H_4$ | 10/100 | 2/100 | 5/100 |
| 2 | $CH_3$ | $CH_3$ | H | $C_6H_4$ | 5/100 | 2/100 | 5/100 |
| 3 | $CH_3$ | $CH_2C_6H_5$ | H | $C_6H_4$ | 0.5/5 | 0.2/5 | 0.5/5 |
| 4 | $CH_3$ | $(CH_2)_3-N\underset{\_\_\_}{\frown}O$ | H | $C_6H_4$ | 12.5/200 | — | 12.5/200 |
| 5 | $C_3H_7$ | H | H | $C_6H_4$ | 20/50 | 20/50 | 20/50 |
| 6 | $C_6H_5$ | H | H | $C_6H_4$ | 25/50 | 12.5/50 | 12.5/50 |
| 7 | $C_6H_5$ | $CH_3$ | H | $C_6H_4$ | 20/50 | 20/50 | 20/50 |
| 8 | $C_6H_5$ | $CH_2C_6H_5$ | H | $C_6H_4$ | 2/10 | 2/10 | 5/10 |
| 9 | H | H | H | $C_6H_4$ | 20/>200 | 10/>200 | 20/>200 |
| 10 | $CH_3$ | H | 5'-$CH_3$ | $C_6H_4$ | 100/200 | 200/200 | 100/200 |
| 11 | $CH_2\!-\!\!-\!\!-\!CH$<br>$\;\;\mid\;\;\;\;\;/$<br>$\;\;CH_2$ | H | H | $C_6H_4$ | — | — | — |
| 12 | $C_2H_5$ | H | H | $C_6H_4$ | 10/100 | 5/100 | 10/100 |
| 13 | $CH_2\!\!<\!\!\begin{array}{l}CH_2-\\CH_2-\end{array}$ | H | (See R) | $C_6H_4$ | 5/50 | 2/50 | 5/50 |
| 14 | $C_6H_{11}$ (cyclohexyl) | H | H | $C_6H_4$ | 10/20 | 5/20 | 10/20 |
| 15 | $CH_3$ | $(CH_3)_3C\overset{O}{\overset{\|}{-}}C$ | H | $C_6H_4$ | 5/100 | 2/100 | 5/100 |
| 16 | H | $CH_3$ | H | $C_6H_4$ | 20/200 | 10/200 | 20/200 |
| 17 | $CH_3$ | $C_2H_5$ | H | $C_6H_4$ | 5/20 | 5/20 | 5/20 |
| 18 | $CH_3$ | n-$C_6H_{11}$ | H | $C_6H_4$ | — | — | — |
| 19 | $CH_3$ | n-$C_{10}H_{21}$ | H | $C_6H_4$ | — | — | — |
| 20 | $CH_3$ | $CH_3\overset{O}{\overset{\|}{C}}-$ | H | $C_6H_4$ | 5/50 | 2/50 | 2/50 |
| 21 | $CH_3$ | $C_6H_5\overset{O}{\overset{\|}{-}}C-$ | H | $C_6H_4$ | 10/50 | 5/50 | 5/50 |
| 22 | $C_6H_6$ | H | $CH_3$ (3' position) | $C_6H_4$ | — | — | — |

In vitro (tissue culture) activity has also been demonstrated against polio, coxsackie A21 and B1, and human rhinovirus (including types 1A, 1B, 2, 3, 5, 13, 14, 15, 39, 41, 51, 998, 1426, 1492, 1662, 4006 and 6579). The compounds of this invention can therefore be used at concentrations of 1 to 200 micrograms per ml in aqueous media, preferably with a surfactant, to decontaminate the in vitro habitat on which such viruses are present, including surfaces such as laboratory glassware, laboratory containers, laboratory working surfaces and similar areas in research laboratories and hospitals, etc.

The following table shows activities of representative compounds against polio 2 and coxsackie A21 virus when tested by the method given earlier.

TABLE IV

| Compound of Example | Activity/Toxicity (µg/ml) | | |
|---|---|---|---|
| | Polio-2 | Coxsackie-A21 | B-1 |
| 1 | 10/>20 | 5/>100 | 20/>80 |
| 2 | 5/>20 | 20/80 | 10/>80 |
| 3 | 0.5/5 | 2.5/5 | 1.25/40 |

The use of the compounds of the invention to form dispersions in water of powdered charcoal was shown as follows: Ten milligrams of Darco G-60 activated carbon was added to each of three solutions contained in 5 ml sample vials:

A. 2.0 ml of deionized water
B. 2.0 ml of an 0.25% solution of 4-acetylbenzo-18-crown-6 oxime in deionized water
C. 2.0 ml of an 0.25% solution of 4'-acetylbenzo-18-crown-6 oxime methyl ether in deionized water The vials were shaken and placed against a thin white card on which two red lines had been scribed 0.25 and 0.50 inches from the bottom. The times at which the lines just first became visible (by light transmitted through the card and through the sample) was noted in each of two trials.

| Sample | Time - Seconds for Top Line Visibility | Time - Seconds for Bottom Line Visibility |
|---|---|---|
| A | 20 | 37 |
| A | 20 | 34 |
| B | 120 | 240 |
| B | 120 | 210 |
| C | 68 | 150 |
| C | 74 | 156 |

Thus the incorporation of only 0.25% of the two crown ether oxime derivatives increased the settling time by factors of 6 and 3 respectively.

A further showing of the effectiveness of the new compounds to suspend particles follows:

Three 15 × 45 mm sample vials were labelled A, B and C and 10 mg of Vulcan 3-R carbon black was added to each. Two ml of water was added to vial A.

A solution of 5 mg of 18-(1-hydroxyiminoethyl)-2,3,5,6,8,9,11,12,14,15-decahydro-1,4,7,10,13,16-benzohexaoxacyclooctadecin(4'-acetylbenzo-18-crown-6 oxime, Example 1 in 2 ml of water was placed in vial B.

A solution of 5 mg of 18-(1-methoxyiminoethyl)-2,3,5,6,8,9,11,12,14,15-decahydro-1,4,7,10,13,16-benzohexaoxacyclooctadecin(4'-acetylbenzo-18-crown-6 oxime-O-methyl ether, Example 2) in 2.0 ml of water was placed in vial C.

All vials were shaken. In all cases uniform black suspensions were obtained.

The vials were then allowed to stand and were observed periodically. After 10 minutes most of the black particles had settled out of upper half of the control vial A. Vials B and C remained completely opaque.

After 3 days nearly all solids had settled out of vial A. Only partial settling was observable in the top quarter of vials B and C. Thus the settling out of suspended particles in test vials B and C in 3 days (72 hours) was less than had occurred in control vial A in 10 minutes; i.e., the rate of settling had been decreased by more than a factor of 400 times using an 0.25% solution of the products of examples 2 and 3 in water.

The nomenclature used by Chemical Abstracts is based on the following ring numbering system

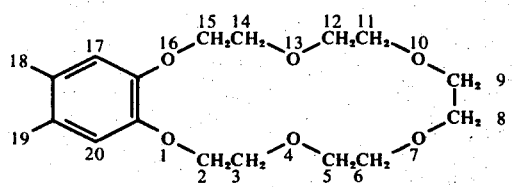

with the substituent(s) on position 18 and any on 19 specified.

I claim:
1. A compound of the formula

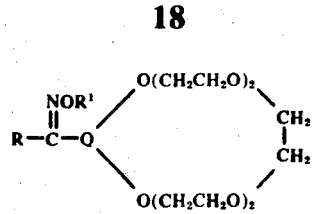

wherein
R is hydrogen, alkyl of 1–10 carbons, aryl of 6–10 carbons, aralkyl of 7–10 carbons, pyridyl, pyrazyl, thienyl, furyl and dioxolyl, and such groups containing up to two substituents of fluorine, chlorine, bromine, nitro, amino or alkoxy of 1–10 carbons;
$R^1$ is hydrogen, alkyl of 1–10 carbons, aminoalkyl of 1–7 carbons, or acyl of 1–10 carbons in which acyl is alkylcarbonyl, arylcarbonyl or aralkylcarbonyl, and such groups containing up to 2 fluorine, chlorine or methoxyl substituents;

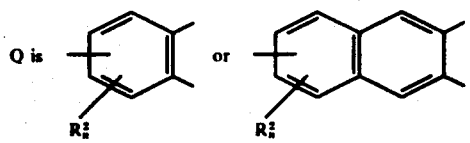

in which
$R^2$ is hydrogen, fluorine, chlorine, bromine, nitro, amino or alkyl of 1–10 carbons; and
$n = 0$ to 2.
2. A compound of claim 1 where R is hydrogen.
3. A compound of claim 1 where R is alkyl.
4. A compound of claim 1 where R is aryl.
5. A compound of claim 1 where $R^1$ is hydrogen.
6. A compound of claim 1 where $R^1$ is alkyl.
7. A compound of claim 1 where $R^1$ is aminoalkyl
8. A compound of claim 1 where $R^1$ is aralkyl
9. A compound of claim 1 where Q is benzo.
10. A compound of claim 1 where Q is naphtho.
11. The compound of claim 1 which is 4'-acetylbenzo-18-crown-6 oxime.
12. The compound of claim 1 which is 4'-acetylbenzo-18-crown-6 oxime O-methyl ether.
13. The compound of claim 1 which is 4'-acetylbenzo-18-crown-6 oxime O-benzyl ether.
14. The compound of claim 1 which is 4'-acetylbenzo-18-crown-6 oxime acetate.
15. The compound of claim 1 which is 4'-butyrylbenzo-18crown-6 oxime.
16. The compound of claim 1 which is 4'-benzoyl 18-crown-6 oxime benzoate.
17. The compound of claim 1 which is 4'-propionylbenzo-18crown-6 oxime O-methyl ether.
18. The compound of claim 1 which is 4'-propionylbenzo-18-crown-6 oxime O-benzyl ether
19. The compound of claim 1 which is 4'-formylbenzo-18-crown-6 oxime.
20. The compound of claim 1 which is 6'-acetyl-2:3-naphtho-18-crown-6 oxime.

* * * * *